US011253297B2

United States Patent
Chen et al.

(10) Patent No.: US 11,253,297 B2
(45) Date of Patent: Feb. 22, 2022

(54) CORTICAL BONE PIN

(71) Applicant: LifeNet Health, Virginia Beach, VA (US)

(72) Inventors: Jingsong Chen, Virginia Beach, VA (US); Thomas Sander, Virginia Beach, VA (US); Dennis Phelps, Virginia Beach, VA (US); Andy Pritchard, Virginia Beach, VA (US); Roberto Bracone, Virginia, VA (US)

(73) Assignee: LIFENET HEALTH, Virginia Beach, VA (US)

( * ) Notice: Subject to any disclaimer, the term of this patent is extended or adjusted under 35 U.S.C. 154(b) by 0 days.

(21) Appl. No.: 16/844,412

(22) Filed: Apr. 9, 2020

(65) Prior Publication Data

US 2020/0229852 A1    Jul. 23, 2020

Related U.S. Application Data

(62) Division of application No. 14/401,195, filed as application No. PCT/US2013/042170 on May 22, 2013, now Pat. No. 10,653,462.

(Continued)

(51) Int. Cl.
*A61B 17/72* (2006.01)
*A61B 17/68* (2006.01)
(Continued)

(52) U.S. Cl.
CPC ...... *A61B 17/7233* (2013.01); *A61B 17/1682* (2013.01); *A61B 17/1686* (2013.01);
(Continued)

(58) Field of Classification Search
CPC ............ A61F 2/4225; A61F 2002/4228; A61F 2002/4233; A61F 2002/4235; A61F 2002/4238; A61F 2002/4241; A61B 17/72
(Continued)

(56) References Cited

U.S. PATENT DOCUMENTS

| 321,389 A | 6/1885 | Schirmer |
| 346,148 A | 7/1886 | Durham |

(Continued)

FOREIGN PATENT DOCUMENTS

| CZ | 220447 B1 | 4/1983 |
| WO | 03007839 A2 | 1/2003 |
| WO | 2011110784 A1 | 9/2011 |

OTHER PUBLICATIONS

European Communication for European Application No. 13 793 254.7, dated Jan. 12, 2016, 9 pages.
(Continued)

*Primary Examiner* — David W Bates
(74) *Attorney, Agent, or Firm* — RatnerPrestia

(57) ABSTRACT

A pin made of cortical bone may be inserted into adjoining bones of a toe to align and secure the bones. The pin may have barbs to prevent migration of the pin. The pin may include a shoulder to further prevent migration of the pin from the bones, to increase the strength of the pin, and to increase the surface area between the bone pin and the host bone. The pin may further include flattened portions on its circumference to aide in rotating the pin during insertion. The pin may be treated to reduce brittleness.

21 Claims, 8 Drawing Sheets

Related U.S. Application Data

(60) Provisional application No. 61/650,364, filed on May 22, 2012.

(51) Int. Cl.
*A61B 17/84* (2006.01)
*A61B 17/16* (2006.01)
*A61F 2/42* (2006.01)

(52) U.S. Cl.
CPC ............ *A61B 17/68* (2013.01); *A61B 17/846* (2013.01); *A61F 2/4225* (2013.01); *A61B 17/7291* (2013.01)

(58) Field of Classification Search
USPC ...................................................... 623/21.19
See application file for complete search history.

(56) References Cited

U.S. PATENT DOCUMENTS

| | | | |
|---|---|---|---|
| 3,805,302 A | 4/1974 | Mathys | |
| 3,990,118 A | 11/1976 | Strickland et al. | |
| 4,262,665 A | 4/1981 | Roalstad et al. | |
| 4,304,011 A | 12/1981 | Whelan | |
| 4,454,699 A | 6/1984 | Strobl | |
| 4,495,380 A | 1/1985 | Ryan et al. | |
| 5,047,059 A | 9/1991 | Saffar | |
| 5,147,363 A | 9/1992 | Harle | |
| 5,417,692 A * | 5/1995 | Goble ................... A61B 17/68 433/173 |
| 5,425,777 A | 6/1995 | Sarkisian et al. | |
| 5,480,447 A | 1/1996 | Skiba | |
| 5,556,379 A | 9/1996 | Wolfinbarger | |
| 5,683,466 A | 11/1997 | Vitale | |
| 5,797,871 A | 8/1998 | Wolfinbarger | |
| 5,820,581 A | 10/1998 | Wolfinbarger | |
| 5,976,104 A | 11/1999 | Wolfinbarger | |
| 5,977,034 A | 11/1999 | Wolfinbarger | |
| 6,024,735 A | 2/2000 | Wolfinbarger | |
| 6,189,537 B1 | 2/2001 | Wolfinbarger | |
| 6,293,970 B1 | 9/2001 | Wolfinbarger et al. | |
| 6,305,379 B1 | 10/2001 | Wolfinbarger | |
| 6,442,806 B1 | 9/2002 | Wesson | |
| 6,534,095 B1 | 3/2003 | Moore-Smith et al. | |
| 6,544,289 B2 | 4/2003 | Wolfinbarger et al. | |
| 6,830,763 B2 | 12/2004 | O'Leary et al. | |
| 7,063,726 B2 | 6/2006 | Crouch et al. | |
| 8,475,456 B2 | 7/2013 | Augoyard et al. | |
| 8,511,962 B2 | 8/2013 | Schuech et al. | |
| 8,551,137 B2 * | 10/2013 | Cohen ................... A61B 17/068 606/213 |
| 8,834,572 B2 | 9/2014 | Averous et al. | |
| 9,072,562 B2 * | 7/2015 | Weiner ............... A61B 17/8883 |
| 9,282,977 B2 * | 3/2016 | Penzimer ........... A61B 17/7291 |
| 9,517,098 B2 | 12/2016 | Anderson | |
| 9,554,914 B2 | 1/2017 | Taylor et al. | |
| 2001/0025199 A1 | 9/2001 | Rauscher | |
| 2002/0022843 A1 | 2/2002 | Michelson | |
| 2003/0032961 A1 * | 2/2003 | Pelo ........................ A61L 27/18 606/232 |
| 2004/0220678 A1 | 11/2004 | Chow et al. | |
| 2007/0147975 A1 | 6/2007 | Homner | |
| 2009/0324360 A1 | 12/2009 | Schuech et al. | |
| 2010/0061825 A1 * | 3/2010 | Liu ...................... F16B 15/0007 411/388 |
| 2010/0130014 A1 | 5/2010 | Nakayashiki et al. | |
| 2010/0217401 A1 | 8/2010 | Beaubien | |
| 2011/0082508 A1 | 4/2011 | Reed | |
| 2011/0257652 A1 | 10/2011 | Roman et al. | |
| 2011/0301652 A1 * | 12/2011 | Reed ................... A61B 17/7291 606/319 |
| 2012/0083791 A1 | 4/2012 | Cheney et al. | |
| 2012/0089197 A1 * | 4/2012 | Anderson .......... A61B 17/7233 606/310 |
| 2013/0053975 A1 | 2/2013 | Reed et al. | |
| 2013/0060295 A1 | 3/2013 | Reed et al. | |
| 2013/0066383 A1 | 3/2013 | Anderson et al. | |
| 2013/0150965 A1 * | 6/2013 | Taylor ................ A61B 17/7291 623/16.11 |
| 2014/0309747 A1 | 10/2014 | Taylor et al. | |
| 2017/0245902 A1 | 8/2017 | Hollis et al. | |

OTHER PUBLICATIONS

Canadian Office Action for Canadian Application No. 2874476, dated Feb. 15, 2016, 4 pages.
European Communication for European Application No. 13 793 254.7, dated Nov. 2, 2017, 4 pages.
European Communication for European Application No. 13 793 254.7, dated Feb. 9, 2017, 4 pages.
European Communication for European Application No. 13 793 257.7, dated Jun. 11, 2018, 5 pages.
Entire patent prosecution history of U.S. Appl. No. 14/401,195, filed, Nov. 14, 2014, entitled, "Cortical Bone Pin.".

* cited by examiner

CORTICAL BONE PIN

RELATED APPLICATIONS

The present Application is a Divisional Application of U.S. patent application Ser. No. 14/401,195, filed on Nov. 14, 2014, entitled "CORTICAL BONE PIN"; which claims the benefit of PCT/US13/042170, filed May 22, 2013, entitled "CORTICAL BONE PIN"; which claims the benefit of U.S. Provisional Application No. 61/650,364 filed May 22, 2012, entitled "CORTICAL BONE PIN"; each of which are hereby incorporated by reference for all purposes.

BACKGROUND OF THE INVENTION

Field of the Invention

The present invention relates to a pin for use in aligning and securing bones, and more particularly, to such a pin made of cortical bone that may be used for aligning and securing bones of a toe of a human patient. The present invention may also be used for aligning and securing bones of a hand, forefoot, or forearm of a patient. In particular, a fractured bone of a hand, foot, or forearm may be treated by inserting a pin according to the present invention into at least one segment of the fractured bone.

Discussion of the Related Art

Certain deformities such as hammer toe result in the bones of a toe being arranged in a highly abnormal manner. In some cases, the treatment for such deformities involves inserting a K-wire (Kirschner wire) through the tip of the toe and penetrating through the bones of the toe so as to align the bones in a more ordinary manner. According to this procedure, the K-wire exits the surface of the skin for a certain period of time. This method suffers from several drawbacks. First, the K-wire is exposed, allowing for the K-wire to slide out of the toe. Another drawback is the insertion point is an open wound, thus raising the possibility of infection.

As another treatment, a metal pin may be inserted through an exposed interphalangeal joint. This method involves the steps of (i) incising at the appropriate joint, (ii) driving a drill pin into the shaft of the appropriate phalanges, (iii) measuring, with a depth gauge, the depths of the intramedullary canals, (iv) selecting a pin of an appropriate length dependent on the measurements of the lengths of the intramedullary canals, (v) inserting the pin into the proximal phalange, and (vi) placing the distal phalange over the pin. This method suffers from the several drawbacks. First, the metal pin is not resorbable nor is it removable. Another drawback is the pin may migrate into one of the phalanges (especially the proximal phalange). This may cause instability and a failure to fuse. In extreme cases, one of the phalanges (especially the distal phalange) may become detached from the pin.

SUMMARY OF THE INVENTION

Accordingly, the present invention is directed to a pin that substantially obviates one or more of the problems in the prior art.

In one aspect of the invention, a pm has an elongated body of a substantially cylindrical shape. The pin may include a raised portion, or a plurality of raised portions, that may be formed of peaks and troughs. Such raised portions are referred to herein as "barb(s)." The barbs may extend around the entire circumference of the pin. In certain embodiments, however, the barbs are located on only a portion of the circumference of the pin. The remainder of the circumference of the pin may be flattened. In certain embodiments, voids are created along the circumference of the barbs to create spokes. The pin may include a protrusion (also referred to as a "shoulder") extending outward from the pin. In some embodiments, the pin is made of cortical bone. In some embodiments, the cortical bone pin is treated to reduce brittleness.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
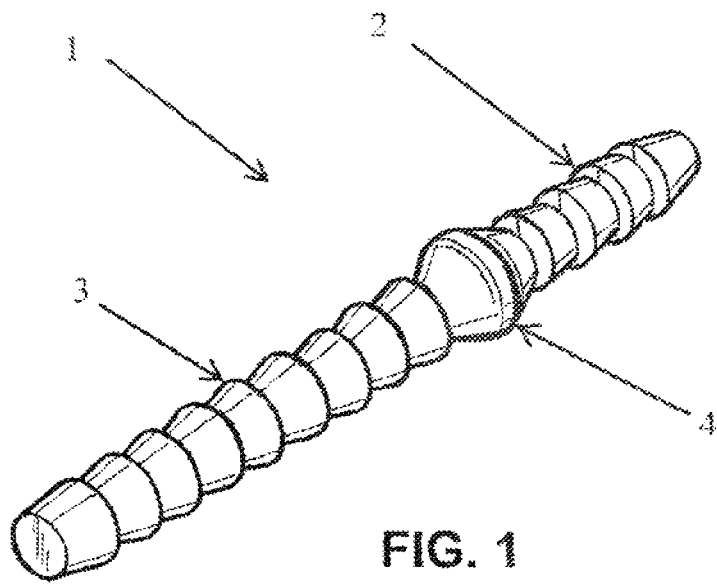
FIG. 1 is a perspective view of a pin according to a first exemplary embodiment of the present invention.

FIGS. 1-4 show a pin 1 according to a first exemplary embodiment of the present invention. As shown in FIG. 1, the pin 1 has a substantially cylindrical shape.

Figure 2:
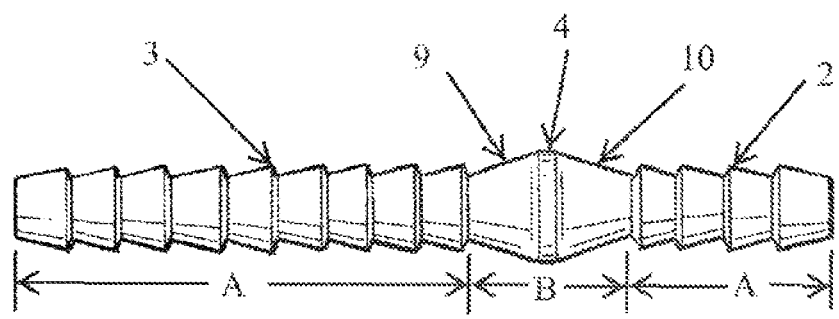
FIG. 2 is a top view of a pin according to a first exemplary embodiment of the present invention.
Figure 3:
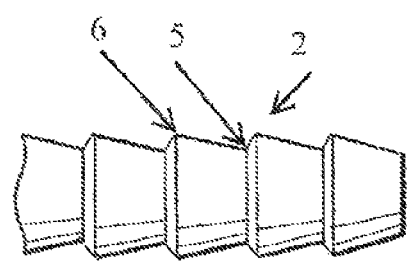
FIG. 3 is a side view of a distal portion of a pin according to a first exemplary embodiment of the present invention.

As shown in FIGS. 1-2, in one embodiment, barbs 2 are provided on the distal end of the pin. Barbs are preferred over threads as the torque required to install a threaded pin may stress the pin to failure. As shown in FIG. 3, the profile of the barbs 2 may be such that, as a barb 2 proceeds from a distal end to a proximal end, the barb 2 slopes gradually from a trough 5 to a crest 6, with an abrupt slope from a crest 6 to a trough 5. This way, the barbs 2 are designed to resist migration of the pin 1 toward a proximal direction after the pin has been inserted into the bone of a toe of a patient. Similarly, the barbs 2 are designed to resist migration of a distal bone of a patient from the pin 1. The barbs 2 may extend completely around the circumference of the pin 1 according to the invention.

Figure 7:
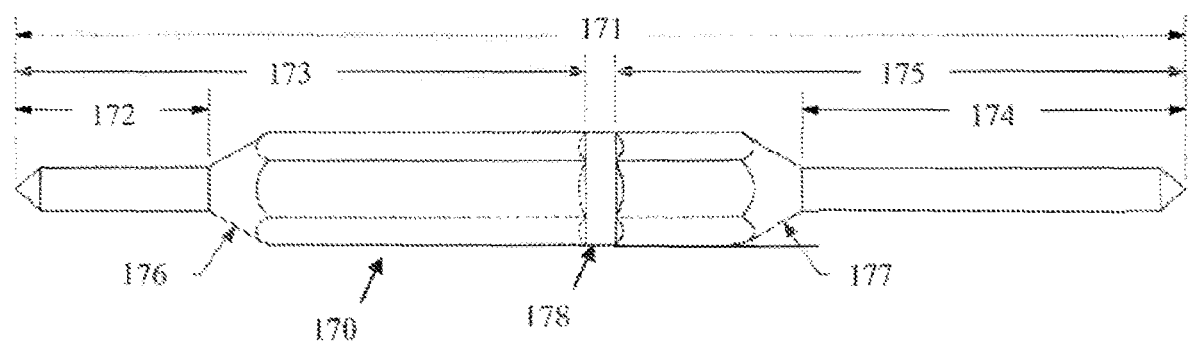
FIG. 7 is a top view of a double-ended drill used to drill out the intermedullary canals of the bones into which a pin according to the present invention is to be inserted.

As shown in FIGS. 1-2, in one embodiment, a shoulder 4 is provided. This shoulder 4 may have a diameter greater than the remainder of the pin 1. For example, the shoulder 4 may have a diameter that is approximately 110%, 115%, 120%, 130%, 150%, 170%, 200%, 250%, 300% or 400% of the diameter of the remainder of the pin 1. The diameter of the remainder of the pin 1 may be approximately 1 mm, 2 mm, 3 mm, or 4 mm. The shoulder 4 may have sloped surfaces 9 and 10 on either side of the apex of the shoulder 4 as depicted in FIGS. 1 and 2. According to the invention, surfaces 9 and 10 may also be contoured, convex, concave, stepped, or irregular to complement the surface area created inside the bone. For example, the internal surface area of the bone may be created and/or shaped by the drilling of the intramedullary canals using a drill bit having various profiles. FIGS. 1, 2 and 7 show a sloped profile; of course, drill bits and shoulder surfaces having other profiles may be employed in other embodiments. In some aspects, pins are designed such that the surface(s) of the pin are complementary to the internal surface area of the bone to maximize, to the extent possible, surface proximity and fusion efficiency. Additionally, the shoulder 4 is designed to prevent migration of the pin 1 into a proximal bone. Thus, it is not necessary that the length of the pin equal the combined lengths of the intramedullary canals of the phalanges. By contrast, in the prior art practice, the length of the pin must be very nearly equal to the combined lengths of the intramedullary canals of the phalanges. In these systems, incorrect selection of the length of the pin may result in pin migration, resulting in instability and failure to fuse. Further, in this application the bone pin undergoes relatively large stress at the proximal bone-bone pin interface. However, according to the invention, because the shoulder 4 has a relatively large diameter, the pin 1 is well suited to undergo the stresses at the proximal bone-bone pin interface. Additionally, as mentioned above, in one embodiment the sloped surfaces 9 and 10 of shoulder 4 increase the surface area of contact between the pin 1 and the host bone, which tends to promote fusion. It being understood that other shoulder profiles may provide improved surface area proximity and fusion efficiency in the case where drill bits having other profiles are employed for example.

Figure 4:
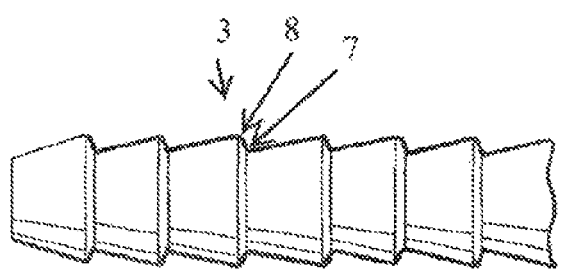
FIG. 4 is a side view of a proximal end of a pin according to a first exemplary embodiment of the present invention.

In one embodiment, barbs 3 are provided on the proximal end of the pin 1. As shown in FIG. 4, these barbs 3 are similar to barbs 2; however, barbs 3 may have a profile such that, as the barb 3 proceeds from a distal end to a proximal end, the barb 3 slopes abruptly from a trough 7 to a crest 8 and slopes gradually from a crest 8 to a trough 7. This way, the barbs 3 are designed to resist migration of the pin 1 toward a distal direction. The barbs 3 may extend completely around the circumference of the pin 1 according to the invention.

In one aspect, the diameters of the features of the proximal portion of the pin may be slightly larger than the diameters of the corresponding features of the distal portion of the pin. In other words, the diameter of crest 8 may be slightly larger than the diameter of crest 6, and the diameter of trough 7 may be slightly larger than the diameter of trough 5.

The pins of the invention may be made from cortical bone. The cortical bone may be human cortical bone or animal cortical bone. It is understood that pins and bone pins are used interchangeably throughout the description and that a pin made of cortical bone is one preferred material of construction for the pin. In addition to cortical bone, other resorbable and biocompatible materials may be used. Additionally, non-metallic synthetics may be used for the pin material. Cortical bone, resorbable and biocompatible materials, and non-metallic synthetics are preferred pin materials compared to metals to promote enhanced fusion.

As described in further detail below, a bone pin according to the present invention may be made and treated according to the following procedures.

In certain embodiments, the bone pin is cleaned according to the methods described in U.S. Pat. Nos. 5,556,379; 5,797,871; 5,820,581; 5,976,104; 5,977,034; and 6,024,735.

The bone pin may be machined by a CNC machine. Alternatively, other manufacturing methods may be used.

In another embodiment, after the bone pin has been cleaned and disinfected, it may be demineralized in accordance with the disclosures of U.S. Pat. Nos. 6,534,095; 6,830,763; 6,189,537; and 6,305,379, all of which are hereby incorporated by reference. This reduces or eliminates the likelihood of disease transmission and/or improves fusion. The demineralization may be a surface demineralization. The surface demineralization may be applied to the whole body or a portion of the bone pin 1, such as the shoulder 4. In some embodiments, the demineralized portion of the bone tissue is at least 10%, 20%, 30%, 40%, 50%, 60%, 70%, 80%, or 90% (v/v %) of the bone tissue. In other embodiments, the demineralized portion of the bone tissue is less than 10%, 20%, 30%, 40%, 50%, 60%, 70%, 80%, or 90% (v/v %) of the bone tissue. This may be accomplished by covering the portions of the bone pin not to be demineralized with acid resistant materials, such as paraffin, with the areas to be demineralized, such as shoulder 4, left exposed. For example, the portions of the bone pin I labeled "A" in FIG. 2 may be covered with a paraffin, while the portion of the bone pin I labeled "B" in FIG. 2 may be exposed. The bone pin may then be treated with an acid solution for a desired amount of time. The acid-resistant material, such as paraffin, may then be removed. In one aspect, this may be accomplished by first refrigerating the bone pin and then detaching the paraffin shell from the bone pin. The absorbed acid may then be removed by rinsing. The depth of demineralization can be controlled by adjusting the type and concentration of the acid solution, and/or the exposure time of the bone pin to the acid solution. The demineralization may also be a full demineralization of a portion of the bone pin, such as the shoulder 4, to enhance bone incorporation and/or create a structural zone with more flexibility.

The above-described "partial demineralization" technique can be applied to other types of cortical or cortical-cancellous bone grafts to control the exact area and depth of demineralization. For example, a cranial bone flap can be processed through such method to be osteoinductive thus promoting new bone formation and fusion to the adjacent host bone, while still maintaining certain mechanical integrity. The treated graft is thus able to withstand surgical fixation through metal plates and screws. The exterior (i.e. abaxial) surface of the cranial bone flap, facing the outside of a body, can be first covered with acid resistant materials such as paraffin. The cranial bone flap may then be treated with acid solution to demineralize the interior (i.e. adaxial) surface of the cranial bone flap, facing the cranial cavity. Of course, as is readily understood by those skilled in the art, acid resistant materials may be employed in various patterns and arrangements in order to demineralize certain portions and leave others untreated as desired.

In another embodiment, the bone pin may be treated in accordance with the disclosures in U.S. Pat. Nos. 6,293,970, 6,544,289, and 7,063,726, all of which are hereby incorporated by reference, which act to improve the preservation of the bone pin. In particular, the following advantages over conventional methods of preservation may be realized. One conventional method of preservation is freezing the bone graft with a liquid. This requires keeping the bone graft in a very cold (such as −80° F.) environment, which may be difficult and expensive. Another conventional method of preservation is freeze-drying the bone graft. However this method results in a brittle bone graft. Further, the surgeon must rehydrate the bone graft prior to insertion into a patient. By contrast, by treating the bone pin in accordance with the disclosures in U.S. Pat. Nos. 6,293,970, 6,544,289, and 7,063,726, the bone pin may be stored at room temperature, the bone pin is not brittle, and a surgeon need only briefly rinse the bone pin prior to insertion into a patient.

Figure 5:
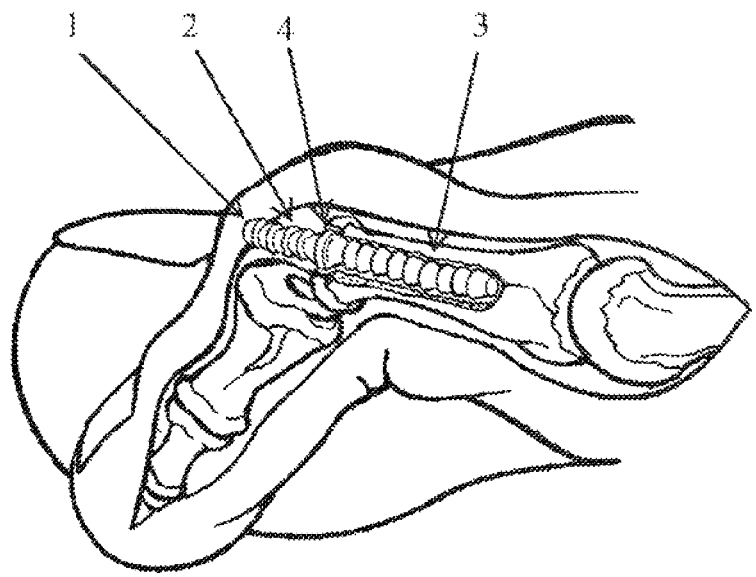
FIG. 5 shows a pin according to a first exemplary embodiment of the present invention partially inserted into the toe of a patient.
Figure 6:
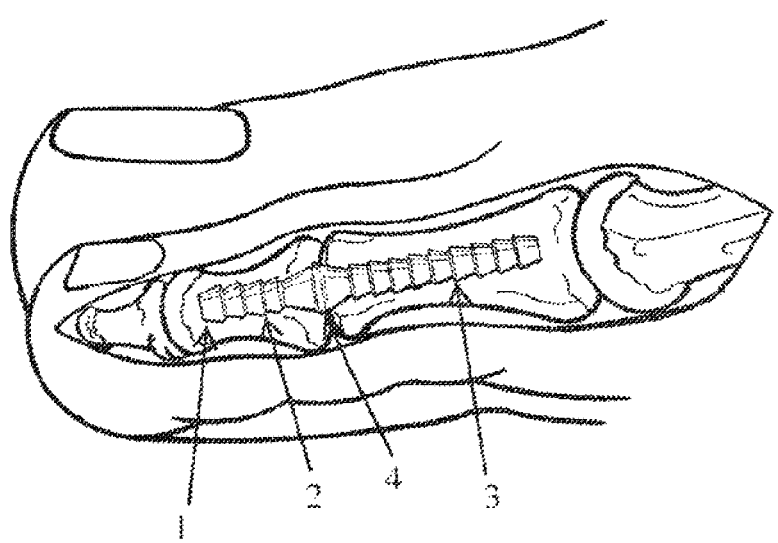
FIG. 6 shows a pin according to a first exemplary embodiment of the present invention fully inserted into the toe of a patient.

An exemplary method of inserting the above-described cortical bone pin into a patient is described with reference to FIGS. 5-8. The method described below is similar to the method described by Dr. Stephen J. Miller in *Hammer Toe Correction by Arthrodesis of the Proximal Interphalangeal Joint Using a Cortical Bone Allograft Pin*, Journal of the American Podiatric Medical Association, Vol. 92, No. 10, pp. 563-69 (2002). First, as with the method described by Dr. Miller, an incision is made above the appropriate joint. The subcutaneous layer is separated. The extensor tendons are retracted or separated, the collateral ligaments are incised, and the joint is brought to the incision. The cartilage from the joint surfaces is then removed. The intramedullary canals of the proximal and distal bones are drilled. A double-ended drill, such as that shown in FIGS. 7-8 (described below), may be used for this step. Migration of the bone pin 1 of the present invention into the proximal phalange is prevented by the shoulder 4. Accordingly, unlike the method described by Dr. Miller, although the surgeon may measure the depths of the intramedullary canals when using a bone pin according to the present invention, it is not necessary to do so. Further, although a surgeon may do so, it is not necessary to cut a pin to the length of the combined measured depths. According to one aspect of the invention, the bone pin 1 may be inserted into the proximal phalange with the shoulder 4 abutting the end of the phalange as shown in FIG. 5. The distal phalange may then be brought up over the bone pin 1 and may be inserted onto the bone pin 1, as shown in FIG. 6. The incision is then closed.

Figure 8:
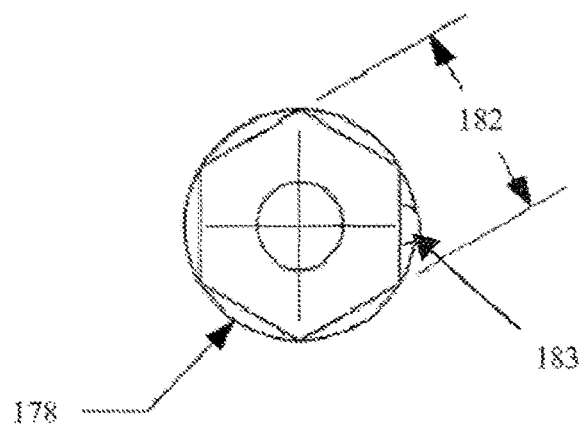
FIG. 8 is an end view of a double-ended drill used to drill out the intermedullary canals of the bones into which a pin according to the present invention is to be inserted.

The double-ended drill referenced in the process above will now be described with reference to FIGS. 7-8. The double-ended drill 170 may include a distal side 173 and a proximal side 175 separated by a hilt stop 178, which may be located at the center of the double-ended drill 170. The drill may include a distal drill 172 and proximal drill 174 and hilt stops 176 and 177. The drill may further include hex flats 182. The drill may also include a detent ball 183 on each side of the drill. The hilt stop 178, hex flats 182 and detent balls 183 may be used in accommodating the drill in standard drill chucks. The overall length 171 of the drill may be from about 3 inches to about 6 inches. The distal drill 172 and proximal drill 174 may include at least one flute (not shown) along their main shafts and auto-centering drill points. The length of the proximal drill 174 may be about 35 mm or less on a drill having an overall length of 3 inches. The length of the distal drill 172 may be approximately one-half the length of the proximal drill 174. The overall lengths of the distal side 173 may be equal to the overall length of the proximal side 175, and these lengths may be independent of the lengths of the distal drill 172 and proximal drill 174. The width of hex flats 182 may be about ¼ inch, ⅜ inch or ½ inch. The face of hilt stops 176 and 177 may be approximately 60° and may include at least one flute (not shown) for cutting a chamber at the insertion point.

In addition to the treatment of hammer toe, the present invention is suitable for other applications, such as the treatment of a fractured bone in a hand, foot, or forearm. In particular, the segments of the fractured bone may be aligned and secured by a cortical bone pin described herein.

Figure 9:
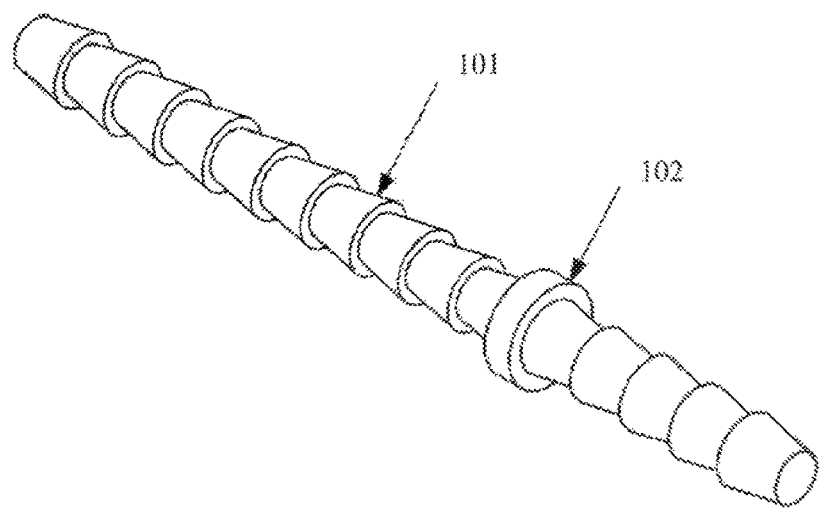
FIG. 9 is a perspective view of a pin according to a second exemplary embodiment of the present invention.

A second exemplary embodiment of the present invention will now be described with reference to FIGS. 9-11. As shown in FIG. 9, a pin according to a second embodiment includes barbs 101 and a hilt 102.

Figure 10:
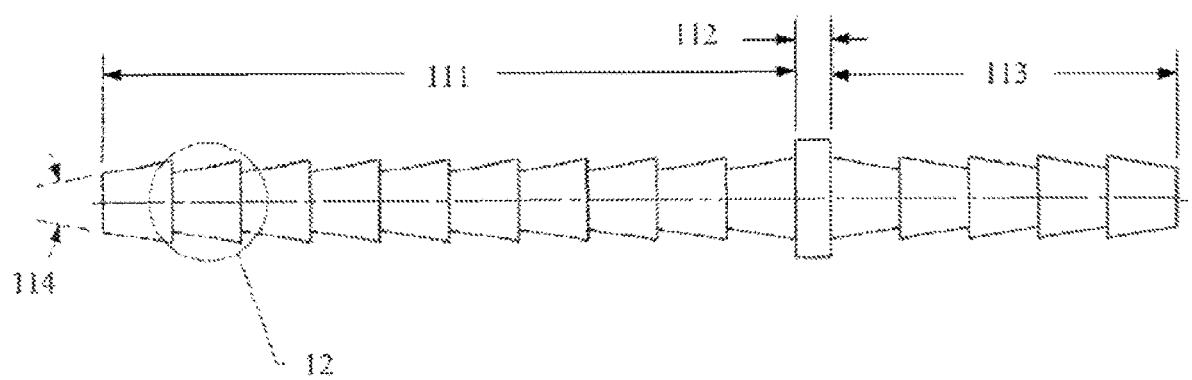
FIG. 10 is a top view of a pin according to a second exemplary embodiment of the present invention.
Figure 11:
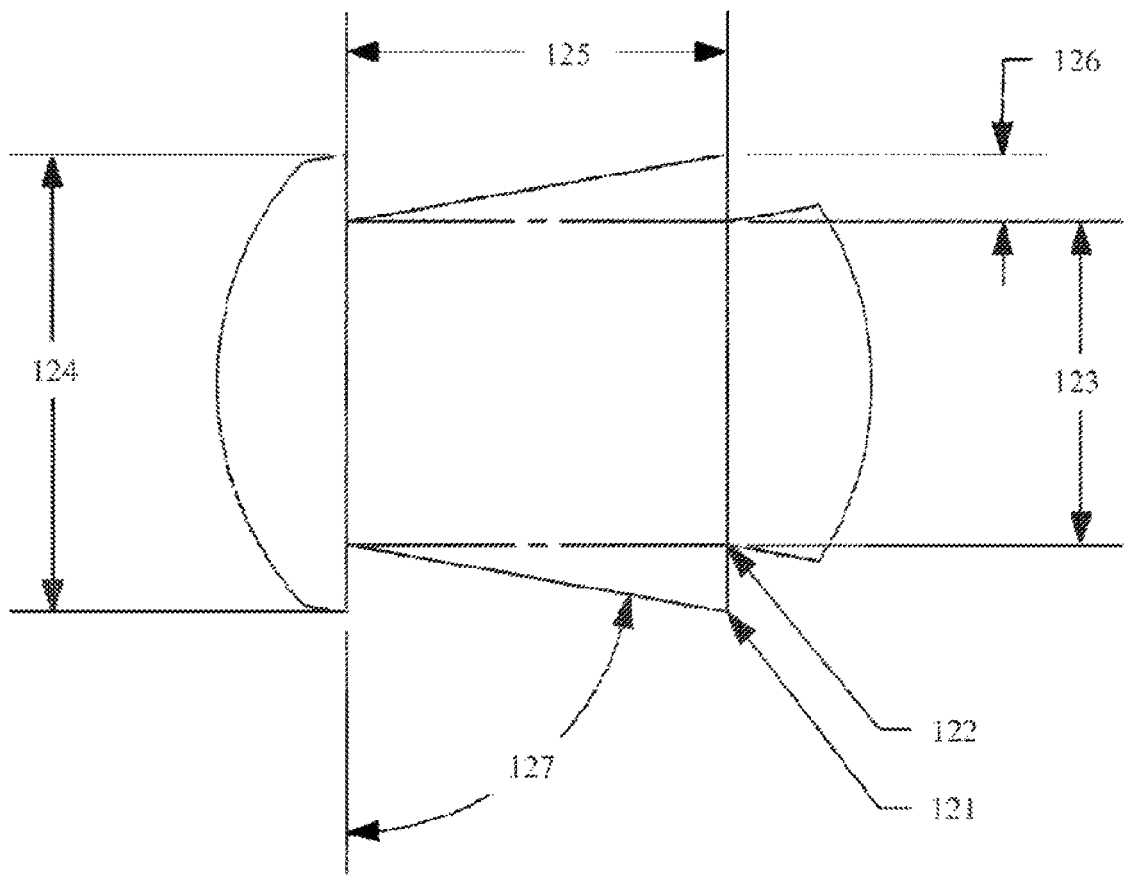
FIG. 11 is a detailed view of a barb of a pin according to a second exemplary embodiment of the present invention.

As depicted in FIG. 10, the pin includes a proximal barb section 111 and a distal barb section 113 separated by the hilt 102. The proximal barb section 111 may be twice the length of the distal barb section 113. The width of the hilt 102 (indicated by 112 in FIG. 10) may be about 0.0 mm to about 5.0 mm. Each barb may have a barb angle 114, being symmetrical to the center line of the pin, of for example approximately 15° to approximately 25°.

Details of the barbs will now be described with reference to FIG. 11. A barb crest 121 may be pointed or dull. A frustum connection 122 which connects each barb with an adjacent barb may be sharp or rounded. A barb minor diameter 123 may be approximately 65% to approximately 75% of a barb major diameter 124, and the barb major diameter 124 may be approximately 130% to approximately 150% of the barb minor diameter 123. Half of the difference between the barb major diameter 124 and the barb minor diameter 123 yields the barb height 126. A barb frustum angle 127 may be obtuse, creating a dull crest, or acute, yielding a sharp and pointed crest. The barb length 125 may be approximately 1.0 mm to approximately mm and may vary from barb to barb on the same pin.

Figure 12:
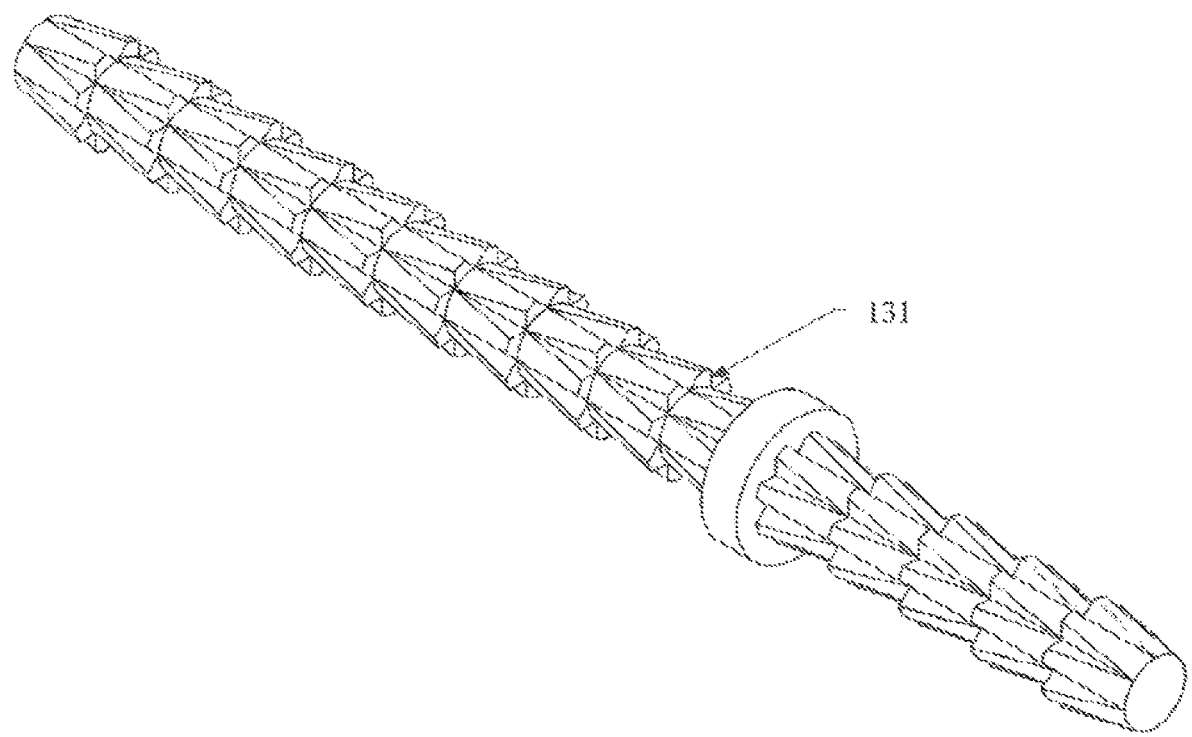
FIG. 12 is a perspective view of a pin according to a third exemplary embodiment of the present invention.
Figure 13:
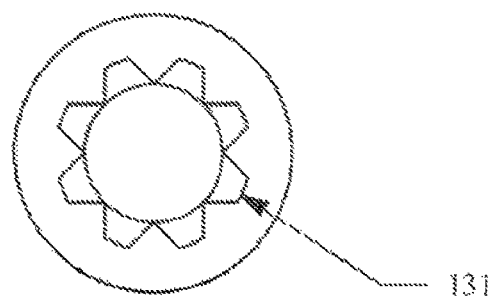
FIG. 13 is an end view of a pin according to a third exemplary embodiment of the present invention.

A third exemplary embodiment of the present invention will now be described with reference to FIGS. 12-13. In the first and second exemplary embodiments, the barbs are depicted as being frustoconical. The outer surface of each barb is continuous and each cross section taken perpendicular to the main axis of the pin may be defined by a circle. In the third exemplary embodiment, by contrast, various voids are created in each barb, resulting in spokes 131.

Figure 14:
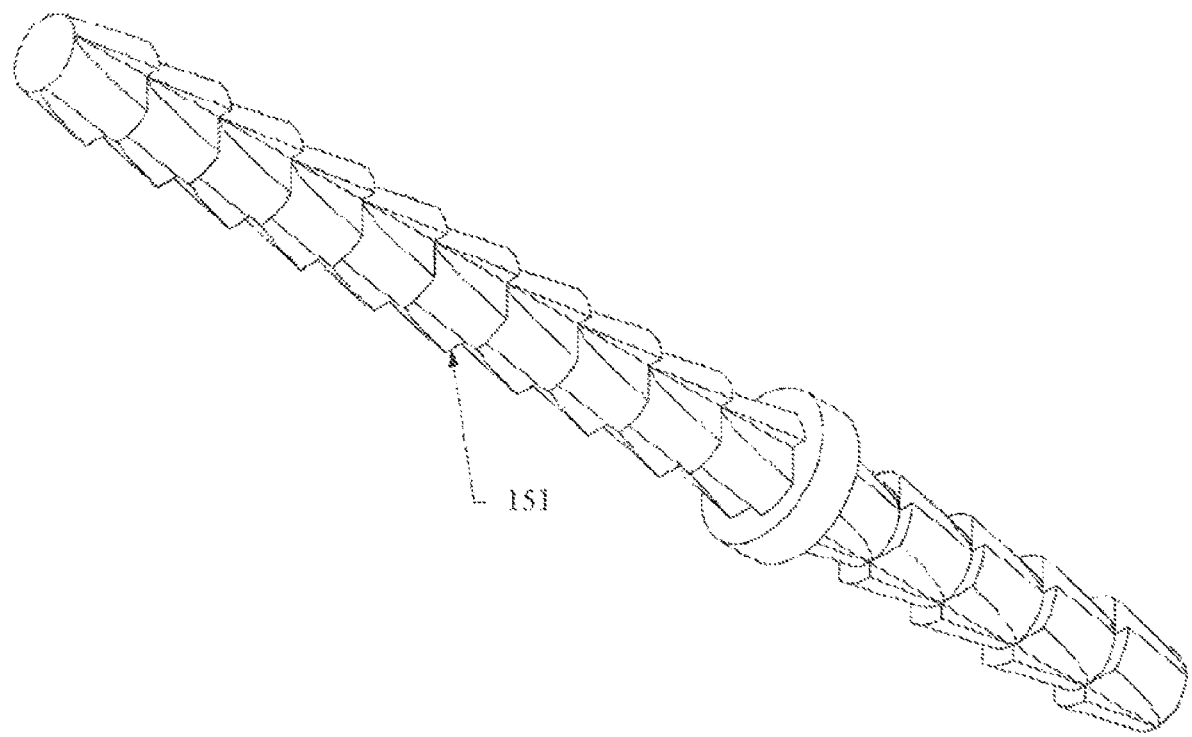
FIG. 14 is a perspective view of a pin according to a fourth exemplary embodiment of the present invention.
Figure 15:
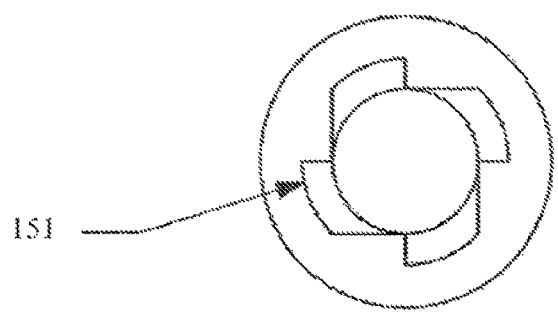
FIG. 15 is an end view of a pin according to a fourth exemplary embodiment of the present invention.

A fourth exemplary embodiment of the present invention will now be described with reference to FIGS. 14-15. Similar to the third exemplary embodiment, various voids may be created in each barb, resulting in spokes 151.

Figure 16:
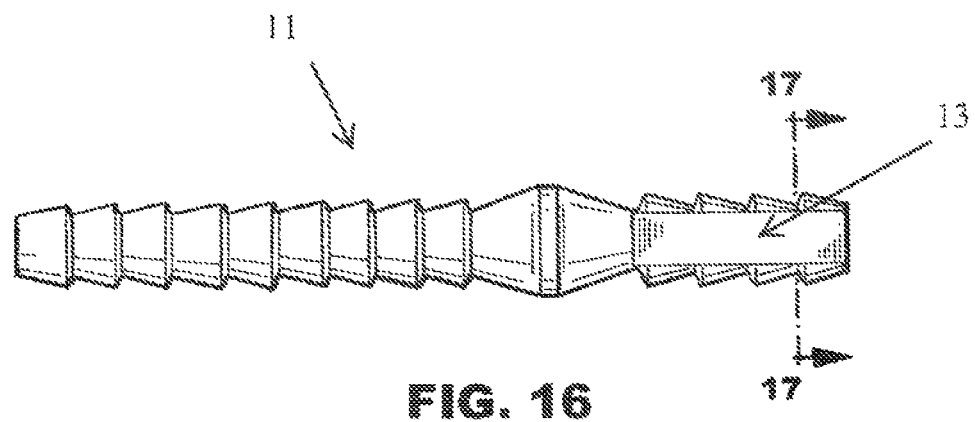
FIG. 16 is a top view of a pin according to a fifth exemplary embodiment of the present invention.
Figure 17:
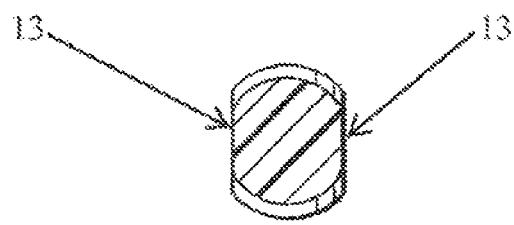
FIG. 17 is a view of a pin according to a fifth exemplary embodiment of the present invention taken along section line 17-17 in FIG. 16.
Figure 18:
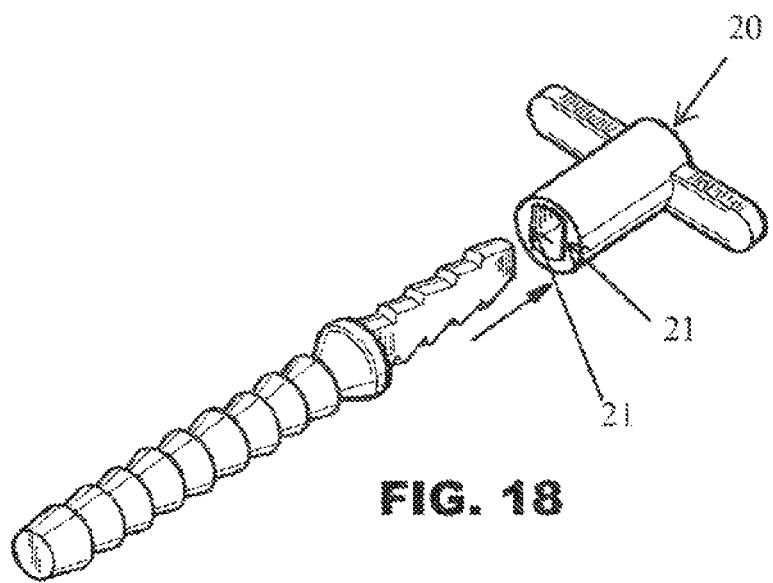
FIG. 18 is a perspective view of a pin according to a fifth exemplary embodiment of the present invention and an insertion tool used to insert a pin according to a fifth exemplary embodiment of the present invention into the bones of a patient.

A fifth exemplary embodiment of the present invention will now be described with reference to FIGS. 16-18. Because the bone pin 11 according to this embodiment is similar to the bone pin 1 according to the first exemplary embodiment, only the differences between bone pin 1 and bone pin 11 will be described. Whereas bone pin 1 is depicted as having a substantially circular cross section across its length, bone pin 11 includes flattened side surfaces 13 as shown in FIGS. 16 and 17. These flattened side surfaces 13 may be located on opposite sides of the distal end of bone pin 11. These flattened side surfaces 13 allow for the use of a tool 20, shown in FIG. 18, during insertion of the bone pin 11 into the proximal phalange. In one embodiment, the tool 20 is substantially cylindrical and substantially hollow. Flattened surfaces 21 may be formed on the inside of the tool and may be designed to engage with the flattened side surfaces 13 of the bone pin 11. According to one aspect, when the tool 20 is rotated, the bone pin 11 rotates during insertion into the proximal phalange.

Other than the specific differences noted above, the second through fifth exemplary embodiments may be similar to the first exemplary embodiment. Thus, for example, the pins according to the second through fifth exemplary embodiments may be made of the same material as the first exemplary embodiment, and may be cleaned, demineralized, and treated according to the same procedures described with reference to the first exemplary embodiment.

It will be apparent to those skilled in the art that various modifications and variations can be made in the pin of the present invention without departing from the spirit or scope of the invention. Thus, it is intended that the present invention cover the modifications and variations of this invention provided they come within the scope of the appended claims and their equivalents.

What is claimed is:

1. A method for using a bone pin, having an elongated body, to align and secure a bone, the method comprising:
   creating an incision in at least one bone segment of a foot, forearm or hand;
   drilling an intramedullary canal between proximate and distal ends of the at least one bone segment;
   inserting the bone pin into the intramedullary canal, wherein the bone pin comprises:
   a proximal portion;
   a distal portion;
   barbs on the proximal portion;
   barbs on the distal portion,
   wherein the barbs on the proximal portion have a profile such that, as the barbs proceed from a distal end to a proximal end of the bone pin, the barbs slope abruptly from a trough to a crest and slope gradually from a crest to a trough, and
   wherein the barbs on the distal portion have a profile such that, as the barbs proceed from a distal end to a proximal end of the bone pin, the barbs slope gradually from a trough to a crest and slope abruptly from a crest to a trough; and
   a shoulder between the proximal portion and the distal portion, wherein the shoulder has an apex and sloped surfaces extending on either side of the apex of the shoulder, and wherein the bone pin has a substantially circular cross section along its entire length.

2. The method of claim 1, wherein the bone pin is inserted into the intramedullary canal of a proximal phalange of a patient to treat hammer toe.

3. The method of claim 1, wherein the bone pin is inserted into the intramedullary canal of a joint of a fractured bone or deformed bone or joint of the hand, foot or forearm.

4. The method of claim 1, wherein the bone pin further comprises flattened surfaces on opposite sides of the bone pin.

5. The method of claim 4, wherein the flattened surface are disposed on the distal portion of the bone pin.

6. The method of claim 1, wherein the bone pin comprises cortical bone.

7. The method of claim 6, wherein the cortical bone is human cortical bone.

8. The method of claim 6, wherein the cortical bone is animal cortical bone.

9. The method of claim 1, wherein the bone pin comprises resorbable materials.

10. The method of claim 1, wherein the bone pin comprises non-metallic synthetic materials.

11. A method for using a bone pin, having an elongated body, to align and secure a bone, the method comprising:
    creating an incision in at least one bone segment of a foot, forearm or hand;
    drilling an intramedullary canal between proximate and distal ends of the at least one bone segment;
    inserting the bone pin into the intramedullary canal, wherein the bone pin comprises:
    a proximal portion;
    a distal portion; and
    a shoulder between the proximal portion and the distal portion,
    wherein the shoulder has a diameter greater than a remainder of the bone pin,
    wherein the shoulder has an apex and sloped surfaces extending on either side of the apex of the shoulder, and
    wherein the bone pin has a substantially circular cross section along its entire length.

12. The method of claim 11, wherein the bone pin is inserted into the intramedullary canal of a proximal phalange of a patient to treat hammer toe.

13. The method of claim 11, wherein the bone pine is inserted into the intramedullary canal of a joint of a fractured bone or deformed bone or joint of the hand, foot, or forearm.

14. The method of claim 11, further comprising barbs on the proximal portion of the bone pin; and barbs on the distal portion, wherein the barbs on the proximal portion have a profile such that, as the barbs proceed from a distal end to a proximal end, the barbs slope abruptly from a trough to a crest and slope gradually from a crest to a trough, and the barbs on the distal portion have a profile such that, as the barbs proceed from a distal end to a proximal end, the barbs slope gradually from a trough to a crest and slope abruptly from a crest to a trough.

15. The method of claim 14, wherein the bone pin further comprises flattened surface on opposite sides of the bone pin.

16. The method of claim 15, wherein the flattened surfaces are disposed on the distal portion of the bone pin.

17. The method of claim 11, wherein the bone pin comprises cortical bone.

18. The method of claim 17, wherein the cortical bone is human cortical bone.

19. The method of claim 17, wherein the cortical bone is animal cortical bone.

20. The method of claim 11, wherein the bone pin comprises resorbable materials.

21. The method of claim 11, wherein the bone pin comprises non-metallic, synthetic materials.

\* \* \* \* \*